United States Patent [19]

Tschesche et al.

[11] Patent Number: 4,595,674
[45] Date of Patent: Jun. 17, 1986

[54] HOMOLOGUES OF APROTININ WITH, IN PLACE OF LYSINE, OTHER AMINOACIDS IN POSITION 15, PROCESS FOR THEIR PREPARATION AND THEIR USE AS MEDICAMENTS

[75] Inventors: Harald Tschesche, Bielefeld; Herbert Wenzel, Muelheim; Rainer Schmuck, Bielefeld; Eugen Schnabel, Wuppertal, all of Fed. Rep. of Germany

[73] Assignee: Bayer Aktiengesellschaft, Leverkusen, Fed. Rep. of Germany

[21] Appl. No.: 711,340

[22] Filed: Mar. 13, 1985

Related U.S. Application Data

[63] Continuation-in-part of Ser. No. 627,943, Jul. 5, 1984.

[30] Foreign Application Priority Data

Jul. 28, 1983 [DE] Fed. Rep. of Germany ....... 3327277
Nov. 3, 1983 [DE] Fed. Rep. of Germany ....... 3339693

[51] Int. Cl.$^4$ .................. A61K 37/64; C07K 7/10
[52] U.S. Cl. .................................. 514/9; 530/324
[58] Field of Search ................. 260/112.5 R; 514/9

[56] References Cited

PUBLICATIONS

Chem. Abstr. vol. 90, 152594x (1979).
Eur. J. Biochem. 61, 443–452, (1976).
Biochemistry, vol. 17, (1978) 1675–1682.
Biochemistry vol. 16, (1977) 1531–1541.
J. Biochem. 81, 647–656 (1977).

*Primary Examiner*—Delbert R. Phillips
*Attorney, Agent, or Firm*—Sprung, Horn, Kramer & Woods

[57] ABSTRACT

The invention relates to homologs of aprotinin with, in place of lysine, other amino acid moieties in position 15, methods for their preparation and their use as proteinase inhibitors.

18 Claims, No Drawings

HOMOLOGUES OF APROTININ WITH, IN PLACE OF LYSINE, OTHER AMINOACIDS IN POSITION 15, PROCESS FOR THEIR PREPARATION AND THEIR USE AS MEDICAMENTS

This is a continuation-in-part of application Ser. No. 627,943 filed July 5, 1984, now pending.

Aprotinin is a known kallikrein-trypsin inhibitor from the organs of cattle. Its structure is known (formula (I). A lysine residue is located in position 15 in the reactive centre of the peptide chain, and this is crucial for the specificity of the inhibitor.

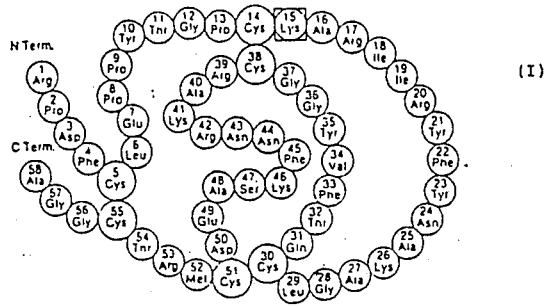

(I)

The present invention now relates to new homologues of aprotinin in which this lysine residue has been replaced by glycine, L-alanine, L-valine, L-leucine, L-isoleucine, L-methionine, L-arginine or L-norleucine, L-norvaline, L-α-aminobutyric acid, dehydroalanine or L-homoserine. The invention also relates to a process for the preparation of these homologues, to intermediates produced in this, and to their use as medicaments.

It is known, from H. Jering and H. Tschesche, Europ. J. Biochem. 61, 443 (1976), that it is possible, using enzymes, to incorporate basic and aromatic amino-acids in place of the missing lysine in de-Lys[15]-aprotinin*, which can be prepared by a sequence of chemical and enzymatic reactions, while the incorporation of other aminoacids in position 15 was not possible by this route. In the following text, aprotinin in which the peptide bond between lysine 15 and alanine 16 has been hydrolysed is designated aprotinin*.

The process, which has been designated enzymatic mutation, by which aprotinin homologues containing phenylalanine, tryptophane and arginine have been prepared, provides single-chain proteins only for the homologues containing phenylalanine and tryptophane.

The arginine[15] derivative is obtained only as a two-chain protein with the arginine 39-alanine 40 bond cleaved and arginine 39 lost.

In the condensation, which has been designated chemical mutation and was carried out using water-soluble carbodiimides, of de-Lys[15]-aprotinin* with the esters of the aminoacids glycine, L-alanine, L-valine, L-leucine, L-methionine and L-arginine, aprotinin* derivatives are obtained, some of which bear the relevant aminoacid ester in position 15 but in which this aminoacid ester has, at the same time, condensed onto all or some of the peripheral carboxyl groups in the side chains of the aspartic acid residues (positions 3 and 50) and the glutamic acid residues (positions 7 and 49) and the terminal alanine (position 58) with the formation of amide bonds [H. R. Wenzel and H. Tschesche, Angw. Chem. 93, 292 (1981)]. In addition, undesired acylureas are formed during the reactions by addition of the carbodiimides onto the carboxyl groups. Thus, after enzymatic resynthesis of the peptide bond between the aminoacid ester in position 15 and alanine 16, according to this literature reference pure aprotinin homologues are not, but mixtures of derivatives of these homologues are, obtained. Hence, pure aprotinin homologues which contain aminoacids other than phenylalanine and tryptophane in position 15 are as yet unknown.

The present invention now makes homologues of this type available. These homologues differ from aprotinin merely by the fact that they bear glycine, L-alanine, L-valine, L-leucine, L-isoleucine, L-methionine, L-arginine, L-α-aminobutyric acid, L-norvaline, L-norleucine, dehydroalanine or L-homoserine in place of lysine in position 15. These homologues can be prepared in good yields in a sequence of suitable chemical and enzymatic reaction steps.

For this purpose, modified aprotinin with the peptide bond between lysine[15] and alanine[16] cleaved (=aprotinin*) is prepared first in a manner known per se. The preparation of aprotinin* can also be carried out without previous reduction of the $Cys^{14}$-$Cys^{38}$ disulphide bridge using the enzymes plasmin or starfish trypsin from *Dermasterias imbricata*. Then the six free carboxyl groups in the molecule are esterified in a known manner using methanolic hydrogenchloride with the formation of the hexamethyl ester of aprotinin*. However, it is also possible to carry out the esterification in analogy to known processes using trialkyloxonium fluoroborate. Moreover, the reaction of aprotinin* with methanol/thionyl chloride is suitable for the preparation of the hexamethyl ester of aprotinin*. In place of methanol, other alcohols having little denaturing activity for proteins are also suitable for the esterification, such as, for example, ethanol and aliphatic (especially alkanoic) alcohols having up to 6C atoms which can also optionally bear substituents such as halogen especially F or Cl and Cyano groups. However, the hexamethyl ester of aprotinin* in which all six carboxyl groups of the aprotinin* molecule are esterified with methanol is preferably used for the further reactions. Where necessary, additional substances in the crude substance produced as a result of incomplete reaction or as a result of side reactions can be separated off in a manner known per se by ion-exchange chromatography on cation exchangers. Cation exchangers bearing carboxyl or sulphonic acid groups, such as CM-cellulose, CM-sephadex, CM-sepharose and SP-sephadex may be used for this purpose. The ion-exchange chromatography is carried out at pH values between 3 and 7, preferably at pH 4.0 to 6.0, using suitable buffer solutions. Examples of buffer solutions of this type are phosphate, acetate, succinate or citrate solutions, the salt content of which is raised continuously or discontinuously during elution. Sodium chloride is preferably used for producing the salt gradients.

Starting from aprotinin* the synthesis of valine-15-aprotinin is represented diagrammatically in FIG. 1. In the diagram of the synthesis shown, the representation of the reaction steps is restricted to that part of the aprotinin molecule related to the active centre (position 15). All the reactions involving the peripheral carboxyl groups (esterification and hydrolysis) are not taken into account in the diagram.

The substances are designated as follows:
(1) Aprotinin*
(2) Hexamethyl ester of aprotinin*
(3) Hexamethyl ester of di-cysteinyl-14,38-aprotinin*
(4) Pentamethyl ester of di-cysteinyl-14,38-aprotinin*
(5) Pentamethyl ester of aprotinin*
(6) Pentamethyl ester of de-lysine-15-aprotinin*
(7) Hexamethyl ester of L-valine-15-aprotinin*
(8) L-Valine-15-aprotinin.

In the hexamethyl ester of di-cysteinyl-14,38-aprotinin* and in the pentamethyl ester of di-cysteinyl-14,38-aprotinin*, the peptide chains cleaved between positions 15 and 16 are still linked covalently via the disulphide bridges of the half-cystines 5/55 and 30/51, but this is not shown in the diagram.

For the selective liberation of the carboxyl group of lysine 15 in the hexamethyl ester of aprotinin*, initially, in a first reaction step, the exposed disulphide bridge between the cysteine residues in positions 14 and 38 is selectively reduced with mercaptoethanol or, preferably, with dithioerythritol in a manner known per se (W. K. Liu and J. Meienhofer, Biochem. Biophys. Res. Commun. 31, 467 (1968)). For this purpose, it is possible to use 5-100 moles of dithioerythritol per mole of hexamethyl ester of aprotinin*, preferably about 50 moles.

The reduction is carried out at pH values from 3 to 7.5, preferably at pH 4.0-6.5, in aqueous buffer solutions. Examples of preferred buffers are succinate, phosphate or acetate buffers which can be 0.005-0.5M, but are preferably 0.1M. To separate off excess dithioerythritol, the reaction solution is filtered, either immediately or after evaporation, through a chromatography column filled with a suitable molecular sieve. It is possible to use volatile buffers having pH values from 2 to 6.5 as the eluting agent, but 0.05-0.1M acetic acid is preferably used as the solvent. However, it is also possible to carry out the liberation of the carboxyl group of the lysine 15 residue without previous removal of the dithioerythritol.

The selective hydrolysis of the hexamethyl ester is advantageously carried out without previous reduction of the Cys 14-38 disulphide bridge. In this case, the oxidation step before adding the carboxypeptidase is dispensable. For the selective hydrolysis of the ester group on the lysine 15 residue in the reduced hexamethyl ester of aprotinin*, reaction is carried out with trypsin which is formylated on the tryptophane residues and which has no amidolytic activity but still has, after appropriate activation, high esterolytic activity with trypsin specificity. The selective hydrolysis is carried out in suitable buffer solutions. Suitable buffers for this purpose are, in particular, phosphate, succinate, acetate or citrate buffers. They can be 0.01-0.5M, preferably 0.1M. The preferred reaction temperature is 25°-37° C., but the hydrolysis can generally be carried out at temperatures from 4° to 50° C. The reaction times are between 1 and 48 hours, preferably 2-10 hours.

The selective hydrolysis of the lysine 15 ester is also possible using unmodified trypsin when organic solvents are added to the reaction solution, since the proteolytic activity of trypsin is likewise diminished by organic solvents, such as dioxane or formamide and 2-chloroethanol. Aqueous buffer solutions which have been diluted with dioxane are particularly suitable for the reactions. A dioxane content between 30 and 75 percent by volume, preferably 40-66 percent by volume, is selected for this purpose. Preferred buffer solutions which may be particularly mentioned are acetate, succinate or phosphate buffers. Their molarity can be 0.01-0.5, preferably 0.05-0.2M, and their pH can be between 2 and 7, preferably between 3.0 and 6.5.

For the selective ester hydrolysis, 0.1-30 mole percent of trypsin is used, preferably 1-10 mole percent. The reaction time is 0.1-10 hours depending on the amount of enzyme used and the pH of the buffer solution. The hexamethyl ester of aprotinin* can advantageously be used for the selective hydrolysis either immediately or after reduction of the Cys 14-38 disulphide bridge.

The synthetic route for the incorporation of valine in position 15 when using the hexamethyl ester of aprotinin* is represented diagrammatically in FIG. 2. As in FIG. 1, the representation is restricted to that part of the aprotinin molecule related to the active centre (position 15); the reactions affecting the peripheral carboxyl groups are not taken into account in the diagram.

The substances are designated as follows:
1. Aprotinin*
2. Hexamethyl ester of aprotinin*
3. Pentamethyl ester of aprotinin*
4. Pentamethyl ester of de-lysine-15-aprotinin*
5. Hexamethyl ester of L-valine-15-aprotinin*
6. L-Valine-15-aprotinin.

After the selective hydrolysis on lysine 15, the Cys 14-38—reduced pentamethyl ester of aprotinin* or the pentamethyl ester of aprotinin* and non-hydrolysed starting material and more acidic components formed as a result of further hydrolysis, and modified trypsin or trypsin are separated by methods customary in protein chemistry. Processes of this type which may be mentioned in this connection are the precipitation of trypsin or modified trypsin with perchloric acid or, preferably, trichloroacetic acid, and the filtration through chromatography columns filled with suitable molecular sieves, the eluting agents which are used being solutions with pH values below 7.0, preferably between pH 1.5 and 3.5, because of the antitrypsin activity still present in the aprotinin* derivative. A preferred solvent is 0.05-0.1M acetic acid, the pH of which has been adjusted to the desired value with hydrochloric acid. The inhibitor fraction resulting from gel filtration, which comprises non-hydrolysed hexamethyl ester of aprotinin*, the desired pentamethyl ester and further hydrolysed derivatives can, where appropriate, be fractionated by ion-exchange chromatography. The fractionation is carried out under conditions analogous to those described above (and in detail in Example 1) for the hexamethyl ester of aprotinin*.

When using the hexamethyl ester of aprotinin* having the Cys 14-38 disulphide reduced, the disulphide bridge between cysteine 14 and 38 is closed by oxidation before splitting off the lysine 15 residue with carboxypeptidase. This oxidation is carried out at pH values from 3.0 to 9.0, preferably at pH 4.5–7.0, by oxidation in a stream of air, and the course of the reaction is monitored using the figures for SH by the method of Ellman.

The lysine 15 is smoothly split off from the pentamethyl ester of aprotinin* using carboxypeptidases, such as, for example, carboxypeptidase Y, but particularly readily with carboxypeptidase B, in buffered solutions at pH values between 3 and 7.5, preferably at pH 4.0–7.0. After acidification of the reaction solution, carboxypeptidase and the pentamethyl ester of de-Lys[15]-aprotinin* are separated in a manner known per se by filtration through molecular sieve columns using buffers with pH values from 1 to 7, preferably 2–5, but particularly with dilute acetic acid as the eluting agent. The pentamethyl ester of de-lysine[15]-aprotinin* is the starting material for the synthesis of the aprotinin homologues and is obtained as a colourless substance on freeze-drying the relevant filtrates.

The introduction of the new aminoacid replacing the lysine 15 residue is carried out by condensation, mediated by carbodiimide, of the pentamethyl ester of delysine[15]-aprotinin* with an ester of the relevant amino-acid in aqueous solutions which, however, can also contain added organic solvents, such as alcohols, dimethylformamide or dimethyl sulphoxide and/or salts.

Water-soluble carbodiimides are particularly suitable for the condensation, such as: N-cyclohexyl-N'-2-(4-morpholinoethyl)-carbodiimide metho-p-toluene-sulfonate, N-tert.-butyl-N'-(3-dimethylaminopropyl)-carbodiimide hydrochloride, N-cyclohexyl-N'-(3-dimethyl-aminopropyl)carbodiimide hydrochloride, N-isopropyl-N'-(3-dimethylaminopropyl)carbodiimide hydrochloride or, preferably, N-ethyl-N'-(3-dimethylaminopropyl)carbodiimide hydrochloride and mixtures of two or more of the carbodiimides listed.

The reactions with the carbodiimides are carried out at temperatures from $-10°$ C. to $+35°$ C., in particular between $0°$ C. and $25°$ C. The pH is maintained between 4.0 and 7.5 in the reaction solution during the reaction by the addition of dilute mineral acid.

In the alkyl esters of the aminoacids used for the synthesis of the aprotinin homologues, the ester alkyl group can be straight-chain, branched or even cyclic, and can contain up to 6C atoms. Thioesters and phenyl esters can also be used, but the methyl esters of the relevant aminoacids are preferably employed.

In the condensations, about 10–1,000 moles of aminoacid ester and about 8–800 moles of carbodiimide are employed per mole of the pentamethyl ester of de-lysine-15-aprotinin*. During this reaction, variable amounts of acylurea(pentamethyl ester of de-Lys[15]-Cys[14]-ureido-aprotinin*) result as a by-product due to addition of the carbodiimides onto the free carboxyl group of the half-cystine residue in position 14. Furthermore, O-arylisourea derivatives are produced as a result of addition of the carbodiimides onto the phenolic hydroxyl groups of the tyrosine residues. These compounds are obtained together with the hexamethyl esters of the aminoacid-15-aprotinin* on gel filtration of the reaction mixtures and are separated off or liberated from the mixture as described below.

The hexamethyl esters of the aminoacid-15-aprotinin* have inhibitory activity. They are formed in yields of 50–95%. The invention also relates to these esters.

The enzymatically controlled intramolecular amide synthesis is favoured in the process according to the invention by the fact that the carboxyl group of the aminoacid in position 15 is activated by the esterification and is present in the undissociated form. Resynthesis is achieved via the acylenzyme, the formation of which is energetically more favourable and takes place $10^3$ times faster when starting from the esterified carboxylic group of the amino acid residue in position 15. It is also important that the steric requirements for intramolecular resynthesis of the peptide bond between the amino acids in position 15 and 16 are provided by formation of the enzyme inhibitor complex which results in a certain tetrahedral deformation of the carboxylic group involved.

Those proteases into whose specificity pocket the side-chain of the aminoacid residue in position 15 fits are particularly useful for the enzymatic formation of the peptide bond between the newly introduced aminoacid in position 15 and alanine in position 16. For example, these are either chymotrypsin or cathepsin G for the homologue containing L-methionine; while they are chymotrypsin, cathepsin G or elastase from granulocytes or pancreas for the homologues containing L-leucine, L-norleucine and L-norvaline, and they are granulocyte elastase for the homologues containing L-valine isoleucine and L-α-aminobutyric acid. The covalent amide bond in the homologues containing L-alanine is produced analogously by pancreatic elastase or trypsin. Trypsin is also suitable for the synthesis of the aprotinin homologues which contain L-arginine or, surprisingly, glycine in position 15.

The enzyme-catalysed synthesis of the peptide bond has the advantage compared with the processes of peptide chemistry that the formation of undesired by-products due to intramolecular or intermolecular condensation is avoided. It can be carried out either with the dissolved enzymes or, advantageously, with carrier-bound enzymes in heterogeneous phase.

Suitable media for the enzymatic condensation are buffer solutions with pH values between 2 and 10. Phosphate, tris(hydroxymethyl)aminomethane or borate buffers or ethanolamine buffer with pH values between 5 and 8.5 are preferably used.

In place of the syntheses under kinetic control using stoichiometric amounts of proteinases with the formation of the 1:1 complexes and their subsequent rapid dissociation to give the enzyme and aprotinin homologues, it is also possible to carry out the synthesis under thermodynamic control using catalytic amounts of enzyme.

The yields of the aprotinin homologues thus synthesised can be increased by adding organic solvents which are miscible with water, such as, for example, glycerol, 1,4-butanediol and dimethylformamide. Some of the ester groups are hydrolysed in alkaline solution during the enzymatic formation of the bond between the aminoacids in positions 15 and 16. Complete hydrolysis takes place on standing in 0.001N–1.0N alkali metal hydroxide solutions, both at $+4°$ C. and at room temperature.

It is unnecessary, particularly when the formation of the peptide bond between the aminoacids in positions 15 and 16 is carried out using carrier-bound enzymes, to purify the aprotinin homologues before hydrolysis. Additional substances present, such as unchanged starting material and, where appropriate, high molecular weight aggregates which have been formed, but particularly the acylureas at the half-cystine 14 residue formed during the carbodiimide condensation, have no inhibitory activity and can be separated off by filtration.

Tyrosine-O-isourea derivatives which are formed to some extent during the carbodiimide condensation can be converted back into underivatised tyrosine residues by treatment with 0.5M hydroxylamine at pH 7.0 with an incubation time of 2–6 hours [compare K. L. Carraway and D. E. Koshland Jr., Biochim. Biophys. Acta 160, 272 (1968)]. On acidifying the suspension to pH values of 1.5 to 3, the aprotinin homologues are liberated from their complexes and pass into the filtrate.

If, in contrast, the 15–16 bond is formed using soluble enzymes, it is advisable to remove the enzymes in a manner known per se by precipitation with acid or by gel chromatography.

The resynthesis of the 15–16 peptide bond in the reactive centre is also to a large extent possible using water-soluble carbodiimides at pH values of 3 to 7, preferably at pH 4.5–5, and it takes place particularly well in the presence of hydroxysuccinimide. However, in this instance, it is necessary to hydrolyse the ester groups, preferably those on the newly introduced amino-acid 15, which can be carried out as described above with sodium hydroxide solution, or, due to their esterolytic activity, with suitable proteinases. The disadvantage of the resynthesis carried out by methods of peptide chemistry compared with the enzymatically catalysed resynthesis are the low yield of desired homologues and the formation of undesired by-products by intramolecular and intermolecular condensation reactions, and addition of the carbodiimide onto the carboxyl groups to give acylureas.

The separation of substances having inhibitory activity from those having no inhibitory activity is also readily carried out by first fractionating, by gel filtration under neutral or alkaline conditions, the reaction solution resulting from the enzymatic condensation. The aprotinin homologue is only eluted in the fractions containing the complex. After adjusting the pH of the solution to values between pH 1 and 4, the enzyme-inhibitor complex dissociates, and the enzyme and the inhibitor can be separated by another gel filtration under acid conditions.

The preferred solvents for these filtrations are acetic acid, formic acid or aqueous mineral acids, or mixtures of these solvents.

It is particularly advantageous for the isolation and purification of the inhibitors according to the invention to utilise their high affinity for proteinases. This is advantageously carried out either after the first step, the chemical condensation, or after the second, the enzymatic reaction, by fractionation using affinity chromatographic procedures. The affinity adsorbents used are usually solid inert substances (carriers) onto the surface of which the relevant enzymes are immobilised by processes known per se. On application followed by elution of the reaction mixtures, the substances having no inhibitory activity are immediately eluted, while substances having inhibitory activity are eluted slowly or are entirely retained. The binding between the carrier-bound enzyme and the inhibitors can then be abolished by varying the pH and/or the salt concentration of the eluting agent, so that the components in the mixture having inhibitory activity are finally obtained in the eluate.

Apart from gel filtration and affinity chromatography, ion-exchange chromatography is particularly suitable for desalting and fractionating the reaction mixtures.

The new aprotinin homologues according to the invention, which only differ from aprotinin by replacement of the aminoacid residue in position 15, are valuable proteinase inhibitors having modified effects and efficacies, which are attributed to the change in the spectra of inhibition.

These changes in the spectrum iof inhibition of the aprotinin homologues according to the invention is due to the replacement of Lys 15 in the active centre of the aprotinin by aminoacids whose side chains fit better into the specificity pockets of the relevant proteinases. According to the results obtained by the groups of Powers and Zimmerman in investigations on the affinity of synthetic substrates and inhibitors for granulocyte elastase, pancreatic elastase, chymotrypsin and cathepsin G, the high inhibitory effect of Leu[15]-aprotinin as well as that of Ile[15]-aprotinin norleucine[15]-aprotinin for all these enzymes, and the relatively high selectivity of the homologue having Val in position 15 for granulocyte elastase, and its inhibition of collagenase, are surprising. It is also surprising that Ala[15]-aprotinin only inhibits the two elastases weakly. The outstanding antitrypsin activity of Gly[15]-aprotinin and the surprising inhibition of tissue kininogenase (kallikrein) are also noteworthy.

The inhibitors according to the invention have biological properties which are superior to those of aprotinin. Their inhibitory effects on the elastases from pancreas and granulocytes, and on cathepsin G and granulocyte collagenase, are particularly advantageous, and these open up new potential therapeutic applications. Important parts are played by pancreatic elastase in pancreatitis, serum elastase in atherosclerosis, and granulocyte elastase in acute and chronic inflammations with damage to connective tissue, in damage to vessel walls and in necrotic diseases and degeneration of lung tissue, for example in emphysema. The part played by lysosomal enzymes, and in particular granulocyte elastase, in inflammatory reactions due to immunological processes, for example rheumatoid arthritis, is equally important.

TABLE 1

Aminoacid composition of aprotinin and some of its homologues, method of Spackman, Stein and Moore, 1958, Anal. Chem. 30, 1190[(1)]

| Amino acid | Aprotinin (theoret.) | Arg[15]—Aprotinin found | theoret. | Gly[15]—Aprotinin found | theor. | Val[15]—Aprotinin found | theor. |
|---|---|---|---|---|---|---|---|
| Asp | 5 | 5.08 | 5 | 4.98 | 5 | 5.03 | 5 |
| Thr | 3 | 2.93 | 3 | 2.95 | 3 | 2.89 | 3 |
| Ser | 1 | 1.38 | 1 | 1.38 | 1 | 1.04 | 1 |
| Glu | 3 | 2.93 | 3 | 2.93 | 3 | 2.79 | 3 |
| Pro | 4 | 3.76 | 4 | 3.81 | 4 | 3.81 | 4 |
| Gly | 6 | 6.00 | 6 | 7.02 | 7 | 6.00 | 6 |
| Ala | 6 | 5.89 | 6 | 6.00 | 6 | 5.79 | 6 |
| Cys | 6 | 5.13 | 6 | 4.88 | 6 | 5.01 | 6 |

TABLE 1-continued

Aminoacid composition of aprotinin and some of its homologues, method of Spackman, Stein and Moore, 1958, Anal. Chem. 30, 1190[(1)]

| Amino acid | Aprotinin (theoret.) | Arg[15]—Aprotinin found | Arg[15]—Aprotinin theoret. | Gly[15]—Aprotinin found | Gly[15]—Aprotinin theor. | Val[15]—Aprotinin found | Val[15]—Aprotinin theor. |
|---|---|---|---|---|---|---|---|
| Val | 1 | 0.62 | 1 | 0.95 | 1 | 1.94 | 2 |
| Met | 1 | 0.65 | 1 | 0.55 | 1 | 0.70 | 1 |
| Ile | 2 | 1.15 | 2 | 1.18 | 2 | 1.36 | 2 |
| Leu | 2 | 1.93 | 2 | 1.89 | 2 | 2.01 | 2 |
| Tyr | 4 | 3.66 | 4 | 3.37 | 4 | 3.58 | 4 |
| Phe | 4 | 4.04 | 4 | 3.68 | 4 | 3.84 | 4 |
| Lys | 4 | 2.58 | 3 | 3.02 | 3 | 2.95 | 3 |
| Arg | 6 | 6.80 | 7 | 5.74 | 6 | 5.96 | 6 |

(1) The molar ratios are related to Gly=6.0, or Ala=6.0 for Gly[15]-aprotinin (o) The figures for isoleucine are found to low after hydrolysis for 18 hours because of an Ile-Ile bond in the molecule.

The inhibitors according to the invention can be characterised by chemical, physicochemical, biochemical and biological properties. The following criteria have been employed:

1. Aminoacid composition

The aminoacid composition was determined by the method of S. Moore, D. H. Spackman and W. H. Stein [Anal. Chem. 30, 1185 (1958)]. The values from aminoacid analysis of some of the aprotinin homologues according to the invention are compiled in Table 1.

2. High-pressure liquid chromatography

The HPLC was carried out using a Hewlett-Packard (HP) model 1084B with a Bio-Sil TSK IEX 530 CM 4×300 mm column (Bio-Rad Labs, Richmond, USA). The flow rate was 1 ml/min using a linear gradient of pH 7.0 buffers containing 0.15M sodium sulphate and 0.6M sodium sulphate (Fixanal 38746 Riedel de Haen) at a column temperature of 40° C. and a pressure of about 50 bar. 20 μl of a solution of 1 mg of aprotinin derivative in 1 ml of water was applied for each run, and detection was at 215 nm and 280 nm. The internal standard used was aprotinin; the reported retention times relate to aprotinin.

3. Electrophoreses

The electrophoreses were carried out under the conditions given by Jering and H. Tschesche [Eur. J. Biochem. 61, 443 (1967)]. However, 7% acrylamide was used in place of 10% acrylamide. The electrophoretic mobilities of the aprotinin homologues were related to that of aprotinin as the standard.

4. Spectrum of inhibition of proteases (a) Elastase inhibition (α) Pancreatic elastase inhibition Crystallised pancreatic elastase (pig) supplied by Nutritional Biochemicals Corp. was used for the inhibition experiments on the aprotinin homologues according to the invention. The substrate employed was succinyl-L-alanyl-L-alanyl-L-alanine p-nitroanilide [J. Bieth et al., Biochem. Med. 11, 350 (1974)]. The cleavage was determined by continuous measurement of the extinction of the liberated p-nitroaniline at 405 nm. In order to ensure maximum formation of the complex, the enzyme and inhibitor were preincubated for 15 min before addition of the substrate. Semiquantitative data on the inhibition of the enzyme for some of the new inhibitors are compiled in Table 2.

(β) Granulocyte elastase inhibition

The isoenzyme mixture used for the inhibition tests was obtained from human granulocytes by the method of K. Ohlsson and I. Olsson [Europ. J. Biochem. 42, 519 (1974)]. Succinyl-L-alanyl-L-alanyl-L-valine p-nitroanilide [H. R. Wenzel et al., Hoppe-Seyler's Z. Physiol. Chem. 361, 1413 (1980)] is particularly suitable as the substrate. Data on the inhibition of granulocyte elastase by some aprotinin homologues according to the invention are listed in Table 2.

(b) Chymotrypsin inhibition

The activity of chymotrypsin was determined photometrically by the method of W. Nagel et al., Hoppe-Seylers Z. Physiol. Chem. 340, 1 (1965) using succinyl-L-phenylalanine p-nitroanilide as the substrate, and the hydrolysis was determined by continuous measurement of the extinction of the liberated p-nitroaniline at 405 nm. The enzyme and inhibitor were preincubated for 15 minutes in the test buffer before adding the substrate. Data on chymotrypsin inhibition for some of the aprotinin homologues according to the invention are contained in Table 2.

(c) Cathepsin G inhibition

The activity of cathepsin G was determined using the β-naphthyl ester of succinyl-L-phenylalanine as the substrate by continuous spectroscopic determination at 328.5 nm of the β-naphthol liberated on enzymatic cleavage. The enzyme reaction is carried out in a 0.25M tris(hydroxymethyl)aminomethane-hydrochloric acid buffer, pH 7.2, which contains 0.05% of Brij 35 and is 0.005M in magnesium chloride. After preincubation of the enzyme and inhibitor in 2.5 ml of the test buffer for 15 min, 0.025 ml of a stock solution of 39.4 mg of substrate in 1 ml of dimethyl sulphoxide is added, and the increase in the extinction at 328.5 nm is determined. The increase in extinction due to spontaneous hydrolysis is subtracted from this extinction. The results for some of the aprotinin homologues according to the invention are contained in Table 2.

(d) Trypsin inhibition

The trypsin activity was determined by the method of H. Fritz et al., [in Methoden der enzymatischen Analyse (Methods of Enzymatic Analysis) edited by H. W. Bergmeyer, 2nd edition, Volume 1, 1011 (1970)] using benzoyl-L-arginine p-nitroanilide as the substrate. The liberated p-nitroaniline was measured in a spectrophotometer at 405 nm. The enzyme and inhibitor were pre-incubated for 15 min before adding the substrate. Data on the inhibition of trypsin by some of the aprotinin homologues according to the invention are to be found in Table 2.

(e) Pancreatic kininogenase inhibition, pancreatic kallikrein

The test enzyme used was pancreatic kallikrein (pig). The enzyme activity was determined using the substrate D-valyl-L-leucyl-L-arginine p-nitroanilide (A. B. Kabi) by the method of T. Dietl et al. [Hoppe-Seyler's Z. Physiol. Chem. 360, 67 (1979)]. The enzyme and inhibitor were preincubated for 15 min before adding the substrate. The hydrolysis was followed by spectrophotometry by determining the liberated p-nitroaniline at 405 nm. Data on the inhibition of kallikrein from pig pancreas are to be found in Table 2.

(f) Collagenase inhibition

Granulocyte collagenase was isolated from human leucocytes by the method of H. W. Macartney and H. Tschesche [FEBS Letters 119, 327 (1980)], and the enzyme activity was determined by the procedure given in this reference. Qualitative indications of the inhibition of granulocyte collagenase by some of the aprotinin homologues according to the invention are given in Table 2.

(g) Factor Xa inhibitors

Human factor X was supplied by Boehringer—5 U in 0.5 ml.

The substrate used was benzoyl-L-isoleucyl-L-glutamyl-glycyl-L-arginine p-nitroanilide (S-2222 supplied by A. B. Kabi). The enzyme activity was determined using the liberation of p-nitroaniline after pre-incubation of the enzyme and inhibitor for 10 min. Table 2 contains data on the efficacy of some of the aprotinin homologues according to the invention.

(h) Plasmin inhibition

The qualitative inhibitory activity on plasmin of some of the aprotinin homologues according to the invention can be seen in Table 2. The determinations were carried out with human plasmin using the substrate D-valyl-L-leucyl-L-lysine p-nitroanilide (S-2251; supplied by A. B. Kabi) after preincubation of the enzyme and inhibitor in a 0.1M tris(hydroxymethyl)aminomethane-hydrochloric acid buffer, pH 7.4, which contained 0.05M sodium chloride, for 10 minutes.

obtained with a single administration of aprotinin in the kaolin and aerosil models.

Design of experiments to demonstrate the antiinflammatory effect on the rat (a) Kaolin-induced inflammatory reaction The inflammatory reaction was induced by intraplantar injection of 0.1 ml of a 10% kaolin suspension into a hind paw of Wistar rats weighing 130–160 g. The aprotinin homologues according to the invention used for treating the inflammatory reaction were dissolved at a concentration of 10–20 mg/ml in a 0.9% sodium chloride solution. The experimental animals were treated by intraperitoneal, intramuscular, subcutaneous or intravenous injection of 0.5–1.0 ml of the solution of the inhibitors and of aprotinin for comparison either prophylactically, that is to say *before* exposure to the agent causing inflammation, or *therapeutically*, that is to say *after* exposure to the agent causing inflammation. The swelling of the inflamed paw, which is a measure of the severity of the inflammatory reaction, was followed over the course of time using the antiphlogmeter of Kemper [F. Kemper and G. Ameln, Z. ges. exp. Med. 131, 407–411 (1959)].

The figure measured 4 hours after exposure to the agent causing inflammation was used to determine the dose-activity relationships.

(b) Aerosil-induced inflammatory reaction

The inflammatory reaction was induced by intraplantar injection of 0.1 ml of a 2% aerosil suspension into a hind paw of Wistar rats weighing 130–160 g. The aprotinin or the aprotinin homologues according to the invention which were used for treating the inflammatory reaction were dissolved at a concentration of 10–20 mg/ml in 0.9% sodium chloride solution. The experimental animals were treated by intraperitoneal, subcutaneous or intravenous injection of 0.5–1.0 ml of the solution of the inhibitors and of aprotinin for comparison 15 h after exposure to the agent causing inflammation. The swelling of the inflamed paw, which is a measure of the severity of the inflammatory reaction, was followed

TABLE 2

Semiquantitative data on the inhibition* of some important proteinases by some of the aprotinin homologues according to the invention.

| Aminoacid moiety in position 15 of the inhibitor | Enzyme | | | | | | | | |
|---|---|---|---|---|---|---|---|---|---|
| | Chymotrypsin | Cathepsin G | Collagenase from granulocytes | Elastase | | Kallikrein | Trypsin | Plasmin | Factor Xa |
| | | | | Granulocytes | pancreatic | | | | |
| Lys (aprotinin) | ++ | (+) | — | (+) | — | +++ | +++ | +++ | — |
| Gly | ++ | n.d. | n.d. | — | — | +++ | +++ | n.d. | n.d. |
| Ala | + | n.d. | ++ | + | + | + | + | n.d. | n.d. |
| Met | +++ | ++ | n.d. | + | + | + | + | n.d. | n.d. |
| Val | + | n.d. | ++ | +++ | + | + | + | n.d. | n.d. |
| Leu | +++ | ++ | n.d. | +++ | +++ | + | + | n.d. | n.d. |
| Arg | ++ | (+) | n.d. | (+) | — | +++ | +++ | +++ | + |

*— no inhibition;
+ weak inhibition;
++ strong inhibition;
+++ very strong inhibition;
n.d. = not determined;
(+) enzyme affinity present In models of acute inflammatory reactions, the aprotinin homologues according to the invention are superior to aprotinin, since, using them, not only is the same effect as with aprotinin achieved in markedly lower doses, but the inflammatory reactions are even significantly inhibited when they are administered several hours after exposure to the agents causing the inflammation. A therapeutic effect of this type cannot be over the course of time using the antiphlogmeter of Kemper. The figure 21 hours after induction of inflammation (=found 6 hours after injection of the aprotinin homologues according to the invention or of aprotinin) was used to determine the dose-activity relationships.

The result of the therapy experiments with the new inhibitors according to the examples demonstrates the efficacy of the aprotinin homologues used in this experimental model, in which aprotinin at the same dose does not inhibit the inflammatory reaction.

By reason of their biological activity, the new inhibitors can be employed for the treatment of, in particular, the following diseases or symptoms:
1. Various forms of shock, in particular shock lung and endotoxin shock, and post-traumatic and post-operative complications,
2. disturbances of blood coagulation,
3. acute and chronic inflammatory reactions, in particular for the therapy and prophylaxis of organic lesions, such as, for example, pancreatitis and radiation-induced enteritis, complex-mediated inflammatory reactions, such as immunovasculitis, glomerulonephritis and types of arthritis; collagenoses, in particular rheumatoid arthritis,
4. types of arthritis caused by metabolism-related deposits (for example gout),
5. degeneration of the elastic constituents of the connective tissue parts of organs, such as in atherosclerosis or pulmonary emphysema,
6. radiation-induced enteritis.

The new active compounds can be converted in a known manner (in analogy to aprotinin) into customary formulations.

In this context, the following formulations should be mentioned as being preferred:
1. Solutions for parenteral administration, for intravenous, intramuscular, subcutaneous injection or for intraarticular and intratumoral injection.
2. Solutions for continuous intravenous infusion,
3. Solutions for use as aerosols for inhalation,
4. solutions, emulsions, ointments, pastes, creams, lotions and powders for external topical application.
5. Combination of various inhibitors having complementary spectra of action.

The concentrations of the new active compounds in appropriate formulations vary within the limits 0.01 to 100 mg/ml of solution, preferably between 0.1 to 10 mg/ml of solution.

The new active compounds can be used in a customary manner, and the following methods of use should be mentioned as being particularly preferred:
(a) parenteral: intravenous, intramuscular, subcutaneous, intraarticular or intratumoral
(b) topical: for example intranasal
(c) oral.

The following daily dosage range can be indicated for the active compounds according to the invention:
0.1–20 mg of active compound per kg of body weight, preferably 1 to 10 mg of active compound per kg of body weight, and the dose is dependent, in particular, on the species to be treated and on the mode of administration.

The active compounds according to the invention can be employed for warm-blooded animals.

EXAMPLE 1

The pentamethyl ester of de-Lys-15-aprotinin*

(a) The hexamethyl ester of aprotinin*

160 mg of aprotinin* (~25 μM) were dissolved in 45 ml of methanol which was 0.1M in hydrogen chloride, and this solution was kept at room temperature (20° C.). Any precipitation which occurred was dissolved by adding further methanol, and the esterification was monitored by HPLC and chromatography on CM sephadex C-25. After about 100 h, the solvent was distilled off in vacuo, and 15 ml of methanol was poured onto the residue and immediately distilled off.

After several repetitions of the dissolution-evaporation procedure, the residue was dissolved in 20 ml of water. On freeze-drying, 150 mg of the hexamethyl ester of aprotinin* was obtained as a colourless substance. Relative electrophoretic mobility: 1.61 (pH 5.0 buffer); relative retention time in HPLC: 2.04 (0.59 for aprotinin*). The substance was dissolved in 10 ml of 0.05M potassium phosphate buffer, pH 4.5, and this solution was applied to a column (2.5–45 cm) filled with CM-sepharose CL-4B Fast Flow which had been equilibrated with the dissolving buffer. The column was developed using a gradient of the buffer of application and a buffer containing 0.8M sodium chloride. The hexamethyl ester of aprotinin* is eluted from the column at a sodium chloride concentration of 0.6–0.7M. The eluates containing the substance were pooled and desalted by ultrafiltration through an Amicon UM-02 membrane, using 0.1M acetic acid. On freeze-drying the retentate, 125 mg of colourless substance were obtained.

(b) The hexamethyl ester of di-cysteinyl-14,38-aprotinin*

104 mg of the hexamethyl ester of aprotinin* (~16 μmol) were dissolved in 12 ml of 0.1M oxygen-free phosphate buffer, pH 5.8. 154 mg of dithiothreitol (1 mmol) were added to this solution. After the reaction solution had stood under an atmosphere of nitrogen for 6.5 hours, the pH was adjusted to 3 with acetic acid. The mixture was filtered through sephadex G-25 (column dimensions: 2.5×100 cm) to remove the dithiothreitol, and the filtrates containing protein were lyophilized 95 mg of colourless substance were obtained.

(c) The pentamethyl ester of di-cysteinyl-14,38-aprotinin*

90 mg (~14 μmol) of substance obtained according to 1(b) were dissolved in 10 ml of 0.1M phosphate buffer, pH 6.75, and 1 ml of a solution of 25 mg of trypsin, which was formylated on the tryptophane residues, in 2 ml of 8M urea solution, pH 8.0, was added.

The reaction solution was kept at 22° C. for 14 h. Then hydrochloric acid was added until the pH was 2.0, and the solution was filtered through a sephadex G-50 column (2.5×120 cm), with 0.1M acetic acid/hydrochloric acid, pH 2.0, as the eluting agent, in order to separate the enzyme and the aprotinin* derivative. On freeze-drying the fractions containing the aprotinin* derivative, 75 mg of colourless substance were obtained.

(d) The pentamethyl ester of aprotinin*, and the pentamethyl ester of de-lysine-15-aprotinin*

A slow stream of air was bubbled through a solution of 70 mg of substance obtained according to 1(c) in 10 ml of 0.1M phosphate buffer, pH 6.25, at 22° C., until the Ellman test had a negative result.

Then 50 μl of a suspension of carboxypeptidase B were added to the reaction solution, and the mixture was kept at 22° C. for 1 h. After addition of 0.75 ml of glacial acetic acid, the reaction solution was filtered through a sephadex G-50 column (2.5×125 cm), using 0.1M acetic acid as the eluting agent, in order to remove carboxypeptidase B and lysine which had been split off. On freeze-drying the fractions containing the pentamethyl ester of the de-lysine-15-aprotinin*, 50 mg of colourless substance were obtained.

EXAMPLE 2

The pentamethyl ester of de-lysine-15-aprotinin*

(a) The pentamethyl ester of aprotinin*

100 mg of hexamethyl ester of aprotinin* obtained according to Example 1(a) are dissolved in 48 ml of 0.1M sodium acetate buffer, pH 3.5. After addition of 50 ml of dioxane, 2 ml of a solution of 30 mg of trypsin (TPCK-treated) per ml of $10^{-4}$N hydrochloric acid were added, and the solution was kept at room temperature for about 2 hours until the reaction was complete (monitoring by HPLC). Then 1 ml of glacial acetic acid was added to the reaction solution which was concentrated to a volume of 10 ml in vacuo. After adjusting the pH to 2.0 with N hydrochloric acid, the solution was filtered through a sephadex G-50 column (2×120 cm) using 0.1M acetic acid hydrochloric acid, pH 2.0, as the eluting agent. The eluates containing the pentamethyl ester of aprotinin* were, after addition of N sodium hydroxide solution to pH 4.5, concentrated to a volume of 10 ml in vacuo.

(b) The pentamethyl ester of de-Lys-aprotinin*

After adding 0.1N sodium hydroxide solution to pH 6.2 to the condensate obtained according to (a), 50 μl of a suspension of carboxypeptidase B was added to the solution. The solution was kept at room temperature for 30 minutes and then 0.5 ml of glacial acetic acid was added. In order to remove the carboxypeptidase, the solution was filtered through a sephadex G-50 column (2×120 cm) using 0.05M acetic acid, the pH of which had been adjusted to 2 using hydrochloric acid, and the eluates containing the aprotinin derivative were, after addition of sodium hydroxide solution to pH 4.0, concentrated to 10 ml in vacuo. This solution was desalted by filtration through a Bio-Gel P-2 column (2×100 cm). On freeze-drying the appropriate eluates, 85 mg of the pentamethyl ester of aprotinin* were obtained.

EXAMPLE 3

L-Valine-15-aprotinin (a) The hexamethyl ester of L-valine-15-aprotinin*

96 mg of N-ethyl-N'-(3-dimethylaminopropyl)carbodiimide hydrochloride (500 μmol) were added to a solution of 13 mg (2 μmol) of the pentamethyl ester of de-lysine-15-aprotinin*, obtained according to Example 2, and 167 mg of L-valine methyl ester hydrochloride (1 mmol) in 7.5 ml of water at 20° C. Using an autotitrator, the pH of the reaction solution was maintained constant at 4.75 by adding 0.1N hydrochloric acid. After 2 h, the low molecular weight substances contained in the reaction mixture were removed by gel filtration of the mixture through a sephadex G-25 column (1.5×100 cm) using 0.1M acetic acid as the eluting agent. On freeze-drying the eluates containing protein, a colourless substance was obtained in quantitative yield.

(b) The pentamethyl ester of L-valine-15-aprotinin

The lyophilisate obtained according to 3(a) was incubated, with gentle shaking, with 12.5 ml of trypsin-sepharose 4B—loading: 5 mg of trypsin per ml of gel—in 15 ml of 0.01M tris(hydroxymethyl)aminomethane/hydrochloric acid buffer, pH 8.5, for 24 h. The pH of the mixture was then adjusted to 1.8 with 0.1N hydrochloric acid, and the affinity adsorbent was removed by filtration and extracted by washing with a total of 20 ml of 0.1M acetic acid/hydrochloric acid, pH 2.0. The filtrate and washings were pooled and, after adjusting to a pH of 4 using N sodium hydroxide solution, the solution was concentrated to a volume of 10 ml in vacuo. The concentrate was desalted by filtration through a sephadex G-25 column (1.5×100 cm). On freeze-drying the eluates containing protein, 13 mg of colourless substance were obtained.

(c) L-Valine-15-aprotinin

The substance obtained in accordance with Example 3(b) was dissolved in 10 ml of 0.001N sodium hydroxide solution. After standing at 21° C. for 12 hours, the solution was neutralised with 0.01N hydrochloric acid and, after addition of 550 mg of hydroxylammonium chloride, was kept at room temperature for 6 hours. The solution was applied to a CM-sephadex C-25 column (2×40 cm) which had been equilibrated with 0.01M borate buffer, pH 8.6. The column was eluted with a linear gradient of the equilibration buffer and the equilibration buffer containing 0.4M sodium chloride. The eluates which inhibited granulocyte elastase, eluted at a concentration of sodium chloride of 0.25M, were pooled and, after concentrating, the solution was desalted by gel filtration through a Bio-Gel P-2 column (1.5×100 cm) using 0.1M acetic acid as the eluant. After freeze-drying, 5.7 mg of valine-15-aprotinin were obtained. (45% based on the pentamethyl ester of delysine-15-aprotinin* employed); relative electrophoretic mobility: 0.54.

EXAMPLE 4

L-Leucine-15-aprotinin 13 mg of the pentamethyl ester of de-lysine-15-aprotinin* (2 μmol) and 92 mg of L-leucine methyl ester hydrochloride (500 μmol) were condensed using 58 mg of N-ethyl-N'-(3-dimethylaminopropyl)carbodiimide hydrochloride (300 μmol) in analogy to the synthesis of valine-15-aprotinin.

The reaction solution was diluted with 50 ml of 0.05M tris(hydroxymethyl)aminomethane/hydrochloric acid buffer, pH 8.5, and 20 ml of α-chymotrypsin-sepharose CL-4B—loading: 7 mg of enzyme per ml of gel—were introduced into the mixture. After gently shaking for 24 h, the affinity carrier was removed by filtration, and the gel was thoroughly washed with the abovementioned buffer and finally with 250 ml of water.

The α-chymotrypsin-sepharose CL-4B was suspended in 50 ml of 0.1M acetic acid, and 0.1N hydrochloric acid was added until the pH reached 1.8. After standing for 20 min, the mixture was again filtered with suction and the carrier was washed with a total of 100 ml of 0.1M acetic acid in several portions.

The combined filtrates were adjusted to pH 3.0 with N sodium hydroxide solution and concentrated in vacuo to a volume of ~5 ml, and the concentrate was neutralised with 0.1N sodium hydroxide solution. After addition of 0.5 ml of 0.05N sodium hydroxide solution, this mixture was allowed to stand at 20° C. overnight, and after 14 h it was neutralised with 0.1M acetic acid. After addition of 300 mg of hydroxylammonium chloride, the solution was kept at room temperature for 4 hours.

The solution was desalted by gel filtration through a sephadex G-25 column (1.5×100 cm), and the eluates containing protein were pooled and freeze-dried. 7.4 mg of a colourless substance (←58%) were obtained; relative electrophoretic mobility: 0.58.

EXAMPLE 5

Glycine-15-aprotinin (a) The hexamethyl ester of glycine-15-aprotinin*

13 mg of the pentamethyl ester of de-lysine-15-aprotinin* (2 μmol) were condensed using 125.5 mg of the glycine methyl ester hydrochloride (1 mmol) with 94 mg (750 μmol) of N-ethyl-N'-(3-dimethylaminopropyl)-carbodiimide hydrochloride, as described in Example 3(a), and the hexamethyl ester of glycine-15-aprotinin* was isolated in quantitative yield after gel filtration as described there.

(b) Glycine-15-aprotinin 0.25 ml of a 0.1M calcium chloride solution, the pH of which had been adjusted to 6.0 with 1N sodium hydroxide solution, and then 60 mg of bovine trypsin (80% pure) (2 μmol) were added to the solution of the substance obtained according to 5(a) in 10 ml of 0.05M phosphate buffer, pH 3.7. After standing at 20° C. for 30 min, the pH of the solution was adjusted to 8.0 with 1N sodium hydroxide solution, and it was filtered through a sephadex G-50 column (2×100 cm) using 0.05M tris(-hydroxymethyl)aminomethane/hydrochloric acid buffer, pH 7.5, as the eluting agent to separate trypsin from the trypsin-pentamethyl ester of glycine-15-aprotinin complex on the one hand and inactive de-lysine-15-aprotinin* derivatives on the other hand. The eluates corresponding to the complex and to trypsin were combined and 2.5 ml of 0.1N sodium hydroxide solution were added. After the reaction solution had stood at 22° C. for 14 hours, it was neutralised with 1M acetic acid and concentrated to a volume of 10 ml in vacuo. 550 mg of hydroxylammonium chloride were added to the concentrate, and the solution was left at room temperature for 4 hours. The pH of the solution was adjusted to 2 with concentrated hydrochloric acid, and the mixture was applied to a sephadex G-50 column (2×100 cm) without previously removing the precipitate which formed. The column was developed using 0.1M acetic acid/hydrochloric acid, pH 2. 8.3 mg (64%) of colourless substance were obtained by freeze-drying the eluates containing the glycine-15-aprotinin after concentrating and desalting by gel filtration through a Bio-Gel P-2 column (1.5×100 cm).

EXAMPLE 6

L-Arginine-15-aprotinin (a) Oligomethyl esters of L-arginine-15-aprotinin 13 mg of the pentamethyl ester of de-lysine-15-aprotinin* (2 μmol) were reacted with 130.5 mg of L-arginine methyl ester dihydrochloride (500 μmol) in the presence of 57 mg of N-ethyl-N'-(3-dimethylaminopropyl)-carbodiimide hydrochloride as described in Example 3(a).

The pH of the solution was then adjusted to 7.5 by addition of 1N sodium hydroxide solution, and 1 ml of a 0.1M calcium chloride solution and 80 ml of 0.05M tris(hydroxymethyl)aminomethane/hydrochloric acid buffer, pH 7.5, were added. After correcting the pH, 20 ml of trypsin-sepharose CL-4B—enzyme content: 5 mg per ml of gel—were introduced into the solution, and the suspension was gently shaken for 15 h. Then the affinity carrier was filtered off, and the gel was washed with 50 ml of the abovementioned buffer and finally with 100 ml of water. The trypsin-sepharose was suspended in 100 ml of 0.1M acetic acid/hydrochloric acid, pH 1.8. After correcting the pH, the mixture was gently shaken for 20 min and again filtered. The affinity gel was thoroughly washed with 100 ml of 0.1M acetic acid/hydrochloric acid, pH 1.8, in several portions.

After adjusting to a pH of 4.5 with N sodium hydroxide solution, the combined filtrates were concentrated to a volume of about 10 ml in vacuo. The concentrate was filtered through a sephadex G-25 column (2×100 cm) using 0.1M acetic acid as the eluting agent. 9.6 mg (76%) of oligomethyl esters of arginine-15-aprotinin were obtained by freeze-drying the eluates containing the protein.

(b) L-Arginine-15-aprotinin

The substance obtained according to 6(a) was dissolved in 10 ml of 0.001M sodium hydroxide solution, and this solution was kept at 20° C. for 24 h. It was then neutralised with 0.1M hydrochloric acid, and 500 mg of hydroxylammonium chloride were added to the solution. After standing the mixture at room temperature for 3 hours, in order to desalt this solution it was filtered through a sephadex G-25 column (2×100 cm) using 0.1M acetic acid as the eluting agent. The eluates containing proteins were concentrated and freeze-dried. 8.2 mg (86%, or 65% based on the pentamethyl ester of de-lysine-15-aprotinin*) of colourless substance having a relative electrophoretic mobility of 1.05 and a relative retention time of 1.13 on HPLC were obtained.

EXAMPLE 7

L-Norleucine-15-aprotinin

The substance obtained by reaction of 13 mg of the pentamethyl ester of de-lysine-15-aprotinin* (2 μmol) and 55 mg of L-norleucine methyl ester hydrochloride (300 μmol) with 83 mg of N-cyclohexyl-N'-[2-(4-morpholino-ethyl]carbodiimide methyl p-toluenesulphonate (200 μmol) in analogy to Example 3(a) was, in order to synthesise the peptide bond between norleucine 15 and alanine 16, incubated in 50 ml of 0.1M tris(hydroxymethyl)aminomethane/hydrochloric acid buffer, pH 8.0, with 20 ml of chymotrypsin-sepharose CL-4B—loading: 7 mg of enzyme per ml of gel—for 6 hours.

The gel was washed with the abovementioned incubation buffer and finally with 100 ml of water. It was then suspended in 50 ml of 0.1M acetic acid/hydrochloric acid, pH 1.8, and the gel and the liquid were separated by filtration. The affinity gel was washed with 100 ml of 0.05M acetic acid/hydrochloric acid, and the combined filtrates were, after adding concentrated ammonium hydroxide solution to pH 4.0, concentrated to a volume of ~10 ml in vacuo. The concentrate was neutralised and, after addition of 550 mg of hydroxylammonium chloride, it was kept at room temperature for 3 hours. To desalt the solution, it was filtered through a Bio-Gel P-2 column (2×100 cm) using 0.1M acetic acid as the eluting agent. The eluates containing proteins were concentrated and freeze-dried. 9.2 mg (71%) of colourless substance were obtained.

EXAMPLE 8

Norvaline-15-aprotinin

The substance mixture obtained by condensation of 13 mg of the pentamethyl ester of de-lysine-15-aprotinin* (2 μmol) and 67 mg of L-norvaline methyl ester hydrochloride (400 μmol) in the presence of 58 mg of N-ethyl-N'-(3-dimethylaminopropyl)carbodiimide hydrochloride (300 μmol) was proceeded up as described in Example 4. In order to form the amide bond between the amino acid residues at 15 and 16, 20 ml of pancreatic elastase-sepharose CL-4B—loading: 4 mg of enzyme per ml of gel—in 0.05M phosphate buffer, pH 5.2, were used. 7.1 mg (60%) of colourless lyophilisate were obtained on continuing workup in analogy to Example 7.

EXAMPLE 9

L-valine-15-aprotinin (a) corresponds to (a) in Example 3

(b) L-valine-15-aprotinin-pentamethyl ester 23 mg of the L-valine-15-aprotinin*hexamethyl ester obtained according to Example 3a were added to a solution of 12,5 mg of leukocyte elastase in 25 ml of 0.05N sodium acetate buffer with a pH of 5.5, which contained 0.1N of sodium chloride. Then the pH value of the reaction solution was adjusted to 7.5 by adding solid tris-(hydroxymethyl)-aminomethane. After adding 50 mg of magnesium chloride hexahydrate to the reaction mixture the pH value was again adjusted to 7.5 and the solution was kept at room temperature for 12 hours. At the end of this period the enzyme was completely inhibited.

The volume of the reaction solution was reduced to about 2 ml using ultrafiltration via an Amicon UM-2 filter and the concentrate was filtered via a column—1×48 cm—filled with Sephadex G-50 "fine" and equilibrated with 0.1 sodium borate buffer pH 7.5 using the equilibrating solution as the eluting agent. Fractions of 2.8 ml were collected. Tubes 12–22 (31 ml–62 ml of the eluate) contained the elastase-val-15-aprotinin-hexamethylester complex and were combined. After concentrating this fraction by ultrafiltration via an Amicon UM-2 filter to a volume of 2 ml N hydrochloric acid was added to the retentate to give a pH value of 1.8. This solution was filtered via a column (1×48 cm) filled with Sephadex G—50 medium using 0.1N acetic acid hydrochloric acid with a pH of 1.8 as the eluting agent, 100 mg of sodium acetate having been initially introduced into each of the tubes used for collecting the eluates. Tubes 12–16 (31 ml–45 ml of the eluate) contained undissociated elastase inhibitor complex; tubes 17–24 (45–67 ml of the eluate) contained the leukocyte elastase and tubes 25–33 (67–92,5 ml) contained the val-15-aprotinin-pentamethyl ester. The contents of tubes 12–24 were combined and after concentration by ultrafiltration to a volume of ~15 ml were again used for the synthesis of val-15-aprotinin-pentamethyl ester. The contents of tubes 25–33 were desalted using a Spectrapor ® dialysis tube by exhaustive dialysis against water. On freeze-drying the retentate 2.8 mg of val-15-aprotinin-pentamethyl ester remained, the relative retention time in the HPLC was 1.87, the relative electrophoretic mobility was 1.75. The amino acid composition corresponded to theory; the results of sequencing over 41 steps confirmed the structure of val-15-aprotinin-pentamethyl ester.

(c) Valine-15-aprotinin 2 mg of val-15-aprotinin-pentamethyl ester were kept in 1 ml of a 0.1M borate puffer solution with a pH of 10.5 which also contained 0.2M imidazole for 60 hours at room temperature. Then the salts were removed by exhaustive dialysis using water and a Spektrapor ® dialysis tube and the retentate was freeze-dried. 1.6 mg of a colourless substance having a relative electrophoretic mobility of 0.80 and a relative retention time in the HPLC of 0.87 was obtained. The amino acid composition can be seen in Table 1.

EXAMPLE 10

L-isoleucine-15-aprotinin (a) L-isoleucine-15-aprotinin*-hexamethyl ester 300 mg (46 μmol) of des-lysine-15-aprotinin*-pentamethyl ester and 800 mg of L-isoleucine-methyl ester (4.41 μmol) were dissolved in 200 ml of ice water. After 10 min. 280 mg of N-ethyl-N'-3-dimethylaminopropyl-carbodiimide hydrochloride (1.41 μmol) were introduced into the mixture and after a further 120 mins. an equal quantity was again introduced. During the reaction the pH value of the solution was kept between pH 4.7 and 5.0 by adding 0.01N hydrochloric acid. The mixture was allowed to react a further 12 hours at 4° C. Then 70 ml of water were added to the reaction solution. The mixture was applied to a CM-sephadex-fast-flow-column and the column was developed with a gradient of 1 l of an 0.05M phosphate buffer having a pH of 5.5 and 1 l of an 0.05M phosphate buffer having a pH of 5.5, which contained 1M of sodium chloride and 10 ml fractions were collected. Fractions 129 to 140 were desalted by ultrafiltration using an Amicon UM-2 membrane. After freeze-drying 92 mg (32%) of a colourless substance were obtained. This substance exhibited high inhibitory activity against granulocytoelastase: relative retention time in the HPLC=1.74 (relative to aprotinin).

(b) L-isoleucine-15-aprotinin-pentamethylester 30 mg of L-isoleucine-15-aprotinin*-hexamethylester obtained according to Example 3a were added to a solution of 25 mg of leucocyteelastase in 25 ml of a sodium acetate buffer of a pH of 5.5 which contained 0.1M of sodium chloride. Then the pH value of the reaction solution was adjusted to 7.5 by adding solid tris-(hydroxymethyl)-aminomethane. After adding 50 mg of magnesium chloride hexahydrate to the reaction mixture the pH value was again adjusted to 7.5 and the solution was kept at room temperature for 12 hours. At the end of this period the enzyme was almost completely inhibited.

The volume of the reaction solution was reduced to about 2 ml by ultrafiltration via an Amicon UM-2-filter and the concentrate was filtered via a column—1×48 cm—filled with sephadex G-50 "fine" and equilibrated with 0.1M borate buffer having a pH of 7.5 using the equilibrating solution as the eluting agent. 2.8 ml fractions were collected. Tubes 12 to 22 (31 ml to 62 ml of the eluate) contained the elastase-Ile-15-aprotinin-pentamethyl ester complex and the contents were combined. After concentrating this fraction by ultrafiltration via an Amicon UM-2 filter to a volume of 2 ml N hydrochloric acid was added to the retentate until a pH value of 1.8 was reached. This solution was filtered via a column (1×48 cm(filled sephadex G-50 "medium" using 0.1M of acetic acid/hydrochloric acid of a pH of 1.7 as the eluting agent; 100 mg of sodium acetate having been previously introduced into each of the tubes used for collecting the eluates. Tubes 12 to 67 ml of the eluate) contained the granulocyte elastase and tubes 25 to 33 (67 to 92.5 ml) the Ile-15-aprotinin-pentamethyl ester. The contents of tubes 12 to 24 were combined and, after being concentrated to a volume of 15 ml by ultra-filtration were reused for the synthesis of Ile-15-aprotinin-pentamethyl ester. The contents of tubes 25 to 33 were desalted with the aid of a Spectrapor ® dialysis tube by means of exhaustive dialysis in the presence of water. On freeze-drying the retentate 4.2 mg of Ile-15- aprotinin-pentamethyl ester remained; the relative retention time in the HPLC was 1.87, the relative electrophoretic mobility was 1.75. The amino acid composition corresponded to theory; the results of sequencing over 31 steps confirm the presence of Ile-15-aprotinin-pentamethyl ester.

(c) isoleucine-15-aprotinin 2 mg of Ile-15-aprotinin-pentamethyl ester were kept at room temperature for 60 hours in 1 ml of an 0.1M borate buffer of a pH of 10.5, which additionally contained 0.2M of imidazole. Then the salts were removed by means of exhaustive dialysis in the presence of water using a Spectrapor ®-dialysis tube and the retentate was freeze-dried, 1.6 mg of a colourless substance were obtained. Using a 0.02M Tris-glycine-buffer pH 9.4 it had a relative electrophoretic mobility of 0.78 and a relative reaction time in the HPLC of 0.87. The amino acid composition corresponded to theory. Isoleucine-15-aprotinin inhibits leucocyte elastase.

What is claimed is:

1. A homolog of aprotitin in which the lysine residue in position 15 in the active centre of the aprotinin inhibitor has been replaced by one of the residues of the aminoacids glycine, L-alanine, L-valine, L-leucine, L-isoleucine, L-methionine, L-arginine, L-α-aminobutyric acid, L-norvaline, L-norleucine, dehydroalanine and L-homoserine.

2. A homolog of aprotinin, in which only the lysine residue in position 15 in the active centre of the aprotinin inhibitor has been replaced by one of the residues of the aminoacids glycine, L-alanine, L-isoleucine, L-valine, L-leucine, L-arginine, L-α-aminobutyric acid, L-norvaline, L-norleucine, dehydroalanine and L-homoserine or alkyl esters of these homologs in which all or some of their additional carboxyl groups in the side-chains of the acidic aminoacids and in the terminal position have, where appropriate, been esterified.

3. A homolog of aprotinin according to claim 1 or 2, in which the lysine residue in position 15 in the active centre of the inhibitor has been replaced by the residue of L-valine.

4. A homolog of aprotinin according to claim 1 or 2, in which the lysine residue in position 15 in the active centre of the inhibitor has been replaced by the residue of L-leucine.

5. A homolog of aprotinin according to claim 1 or 2, in which the lysine residue in position 15 in the active centre of the inhibitor has been replaced by the residue of L-norleucine.

6. A homolog of aprotinin according to claim 1 or 2, in which the lysine residue in position 15 in the active centre of the inhibitor has been replaced by the residue of L-norvaline.

7. A homolog of aprotinin according to claim 1 or 2, in which the lysine residue in position 15 in the active centre of the inhibitor has been replaced by the resiue of L-α-aminobutyric acid.

8. A derivative of aprotinin in which the peptide bond between the lysine-15 residue and the alanine-16 residue is open and in which only the carboxyl group on the lysine 15 is free, all other carboxyl groups in the side-chains of the aspartic acid residues (positions 3 and 50) and of the glutamic acid residue (positions 7 and 49) and of the C-terminal alanine (position 58) bearing alkyl ester groups.

9. A derivative according to claim 8, in which the ester groups are methyl esters.

10. A derivative of aprotinin having a peptide bond on alanine-16 cleaved, in which the lysine-15 residue is missing, and the carboxyl groups in the side-chains of the aspartate residues—3 and 50—and the glutamate residues—7 and 49—and the C-terminal alanine—5-8—bear alkyl esters, and only the carboxyl group on the half-cystine residue 14 is non-esterified.

11. A derivative according to claim 10, in which the alkyl ester group is a methyl group.

12. A pharmaceutical proteinase inhibiting composition containing as an active ingredient a proteinase inhibiting amount of a compound of claim 1 together with an inert pharmaceutical carrier.

13. A pharmaceutical proteinase inhibiting composition of claim 12 in the form of a sterile or physiologically isotonic aqueous solution.

14. A proteinase inhibiting medicament in dosage unit form comprising an effective proteinase inhibiting amount of a compound of claim 1 and an inert pharmaceutical carrier.

15. A proteinase inhibiting medicament of claim 14 in the form of tablets, pills, dragees, capsules, ampoules or suppositories.

16. A method of providing proteinase inhibition which comprises administering to a warm-blooded animal, an effective proteinase inhibiting amount of a compound of claim 1 in admixture with an inert pharmaceutical carrier.

17. A method according to claim 16 wherein the active compound is administered in an amount of 0.1 to 20 mg per kg body weight per day.

18. A method according to claim 16 wherein the active compound is administered in an amount of 1 to 10 mg per kg body weight per day.

* * * * *